United States Patent [19]  [11] 4,292,432
Ono et al.  [45] Sep. 29, 1981

[54] NOVEL ALDOL DERIVATIVES AND PRODUCTION THEREOF

[75] Inventors: Keiichi Ono, Osaka; Akihiko Sugie, Toyonaka; Hajime Kawakami, Takarazuka; Junki Katsube, Toyonaka, all of Japan

[73] Assignee: Sumitomo Chemical Company, Limited, Osaka, Japan

[21] Appl. No.: 117,981

[22] Filed: Feb. 4, 1980

[30] Foreign Application Priority Data

Feb. 9, 1979 [JP] Japan .................................. 54/14690

[51] Int. Cl.³ .................. C07D 317/12; C07D 319/08; C07D 339/06
[52] U.S. Cl. ............................... 549/35; 260/340.5 P; 260/340.7; 260/340.9 P; 568/343; 568/374; 568/443; 568/445
[58] Field of Search ............... 568/343, 443, 445, 374; 260/340.9 P, 340.5 P, 340.7; 549/35

[56] References Cited

U.S. PATENT DOCUMENTS 3,338,969  8/1967  Muller et al. ...................... 568/343
4,191,660  3/1980  Schreiber et al. ................... 568/343

OTHER PUBLICATIONS

Wagner et al., Synthetic Organic Chemistry, p. 174 and p. 288.
Nielsen et al., Organic Reactions, vol. 16, p. 47.
Sugie et al., Tetrahedron Letters, pp. 2607–2610, 1979.
Nicolaou et al., J.C.S. Chemical Communications, pp. 1067–1068, (1978).
Shibasaki et al., Tetrahedron Letters, pp. 432–437, 1979.
Kojima et al., Tetrahedron Letters, pp. 3742–3747, 1978.
Morton et al., J. Org. Chem., vol. 44, No. 16, 1979, 2880–2887.
Shibasaki et al., Chemistry Letters, pp. 1299–1300, 1979.

Konishi et al., Chemistry Letters, pp. 1437–1440, 1979.

Primary Examiner—Henry R. Jiles
Assistant Examiner—Jane T. Fan
Attorney, Agent, or Firm—Stevens, Davis, Miller & Mosher

[57] ABSTRACT

A process for producing novel aldol derivatives of the formula,

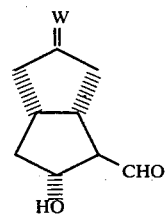

wherein C=W is a carbonyl group or a protected carbonyl group which comprises reacting a compound of the formula:

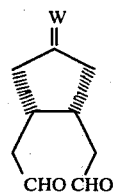

wherein C=W is as defined above in the presence of an acid or a base at a temperature ranging from −70° C. to room temperature. The novel aldol derivatives of the above formula are useful as intermediate for producing methanoprostacyclin derivatives which are useful medicines for prevention of thrombosis.

4 Claims, No Drawings

NOVEL ALDOL DERIVATIVES AND PRODUCTION THEREOF

The present invention relates to novel aldol derivatives which are very useful as intermediates for methanoprostacyclin derivatives, and a novel process for producing the same.

The novel aldol derivatives provided by the present invention are those represented by the formula [I]:

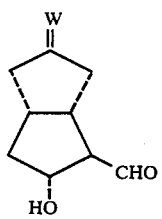

wherein C=W is a carbonyl group or a protected carbonyl group.

The novel process for producing the aldol derivatives [I] involves the intramolecular aldol cyclization of the dialdehyde derivatives of the formula:

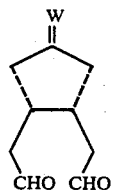

wherein C=W is as defined above.

A tremendous amount of research in synthetic organic chemistry, pharmacology and clinical application of prostaglandins has been performed since discovery of prostaglandins.

In 1976, J. Vane of the Wellcome foundation reported isolation and biological effect of prostacyclin [PGI$_2$] (A) [(S. Moncada, R. Gryglewski, S. Bunting, and J. R. Vane, Nature (London), 263, 663 (1976)].

PGI$_2$, which is shown below, inhibits aggregations of blood platelets and is expected to be useful for prevention of intravascular thrombosis, cerebrovascular thrombosis, and transient ischemic episodes.

However, PGI$_2$ may not be used as a medicine owing to its instability.

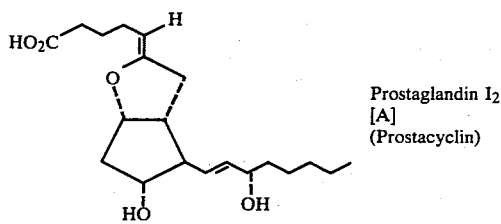

Prostaglandin I$_2$ [A] (Prostacyclin)

In the course of our study seeking novel PGI$_2$ analogs, the present inventors formed as novel PGI$_2$ analogs, the methanoprostacyclin [B] and its congeners [Tetrahedron Letters, 2607 (1979)], which were found to have potent activities similar to PGI$_2$. Moreover the methanoprostacyclin [B] and its congeners were found to be much more stable as compared with PGI$_2$ itself, and thus, these novel methanoprostacyclin derivatives can be used as practically useful medicines for prevention of thrombosis, especially for prevention of platelet thrombosis induced by the use of prosthetic devices such as artificial heart valves.

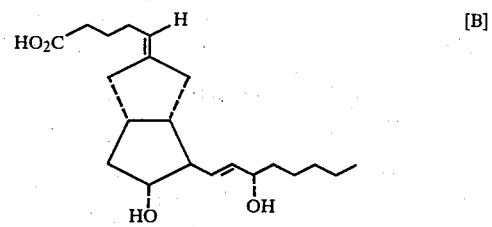

As for the synthesis of the methanoprostacyclin [B], two other approaches have also been published from other research groups [Tetrahedron Letters, 433 (1979), J.C.S. Chemical Communications 1067 (1978), Tetrahedron Letters 3743 (1978)]. But, by any of the synthetic approaches stated above, the methanoprostacyclin [B] was very hard to prepare industrially, since the known syntheses were all suffering from some hardships (too many steps or low availability of the starting materials).

Thus, it has been strongly desired to develop more efficient and more advantageous synthetic approaches for the said methanoprostacyclin derivatives.

As the result of our study, the present inventors have found an efficient process for the synthesis of the aldol derivative [I], and the present inventors have also found that this aldol derivative [I] could be converted efficiently to the objective methanoprostacyclin [B] in only four steps without the protection of its hydroxyl group as shown in the following schema:

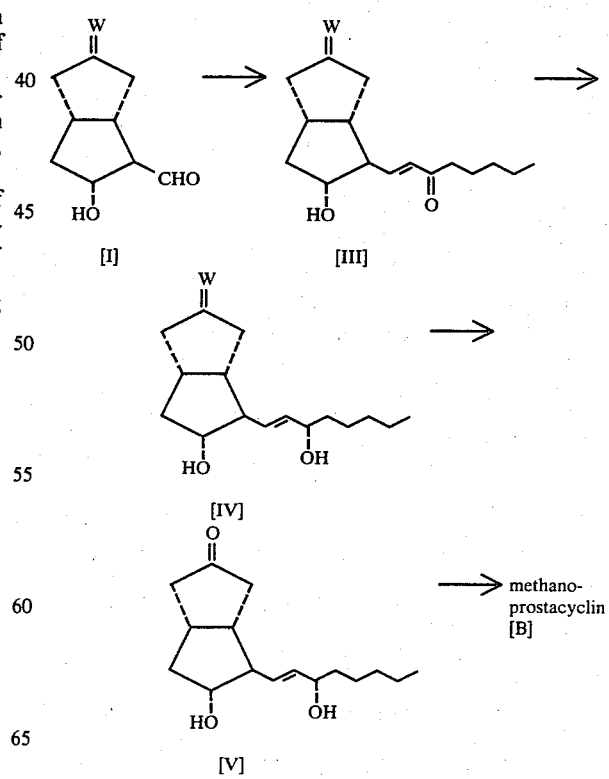

wherein C=W is as defined above.

In the presebnt aldol cyclization of the dialdehyde derivative [II], the desirable one stereoisomer was obtained with good yields and high purity.

On the other hand, the starting material [II] was provided by oxidative cleavage of the olefin derivative [VI] as described below, which could be easily obtained from the industrially available, cis-4-cyclohexene-1,2-dicarboxylic anhydride by the known procedures [e.g. J.O.C. 41 2238 (1978)].

Thus, the present invention has provided an efficient and advantageous synthesis of the methanoprostacyclin and it congeners.

An object of the present invention is to provide the novel aldol derivative [I] which is useful as an intermediate for the production of the methanoprostacyclin and its congeners.

Another object of this invention is to provide a novel and excellent synthetic method for producing the aldol derivative [I].

According to the present invention, the aldol derivative [I] can be produced advantageously by reacting an olefin derivative of the formula:

[VI]

wherein C=W is a carbonyl group or a protected carbonyl group (e.g. W is an oxygen atom; ethylenedioxy group, an ethylendithio group, a 1,3-propane dioxy group, 2,2-dimethyl-1,3-propanedioxy group, a 1,2-phenylenedioxy group, two methoxy groups) with an oxidizing agent to give a dialdehyde derivative of the formula:

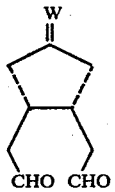

[II]

wherein C=W is as defined above, followed by the intramolecular cyclization in the presence of an acid or a base.

The process of the present invention will be illustrated below in detail according to the sequence of the reaction steps.

STEP 1

Production of the dialdehyde derivative [II]

Oxidation of the olefin derivative [VI] into the dialdehyde derivative [II] can be accomplished by treatment with sodium metaperiodate in the presence of a catalytic amount of osmium tetroxide in an inert solvent at a range of the temperature from 0° C. to room temperature. Examples of the inert solvent include water, ethers (e.g. dioxane, tetrahydrofuran) and aqueous ethers.

The dialdehyde derivative [II] can be also obtained by ozonization at a range of temperature from −80° C. to −30° C., followed by reductive cleavage with dialkyl sulfide, triphenylphosphine, sodium bisulfite, zinc or the like, or by catalytic hydrogenation in the presence of palladium on charcoal.

Examples of the inert solvent for ozonization include alkanols (e.g. methanol, ethanol), halogenated hydrocarbons and ethers.

Reduction of an ozonide may be accomplished by a, per se, conventional procedure at a range of temperature from −30° C. to room temperature.

STEP 2

Aldol condensation of the dialdehyde [II] into the aldol derivative [I] is carried out in the presence of an acid or a base in an inert solvent such as water, alkanols, aqueous alkanols, ethers, and esters at a temperature ranging from −70° C. to room temperature.

Examples of the suitable base are alkali hydroxide [e.g. potassium hydroxide, sodium hydroxide, lithium hydroxide, magnesium hydroxide, barium hydroxide zinc hydroxide], alkali carbonate, alkali hydrogen carbonate and triethylamine, and as the acid, it is preferable to use mineral acids or organic acids.

Specific examples of the aldol derivative [I] are as follows:

2-β-formyl-3-α-hydroxy-7,7-ethylenedioxycis-bicyclo[3,3,0]octane

2-β-formyl-3-α-hydroxy-7,7-propanedioxycis-bicyclo[3,3,0]octane

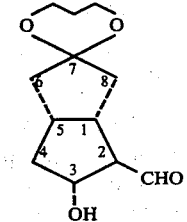

2-β-formyl-3-α-hydroxy-7-oxo-cis-bicyclo[3,3,0]-octane

2-β-formyl-3-α-hydroxy-7,7-dimethoxy-cis-bicyclo[3,3,0]octane

2-β-formyl-3-α-hydroxy-7,7-ethylenedithiocis-bicyclo[3,3,0]octane

2-β-formyl-3-α-hydroxy-7,7-(2,2-dimethylpropanedioxy)-cis-bicyclo[3,3,0]octane

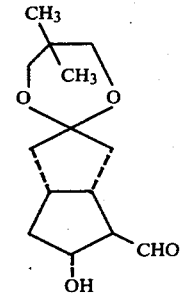

2-β-formyl-3α-hydroxy-7,7-phenylenedioxy-cis-bicyclo[3,3,0]octane

Practical and presently preferred embodiments of the invention are illustratively shown in the following examples without limiting the scope of the invention in any way.

EXAMPLE 1

A few milligrams of osmium tetraoxide were added to a solution of 8,8-ethylenedioxy-cis-bicyclo[4,3,0]non-3-ene (1.0 g), water (20 ml) and dioxane (60 ml).

The mixture was stirred for 5 min at room temperature, and to this mixture was added 2.2 g of sodium metaperiodate.

The mixture was further stirred for 20 min. at the same temperature. This reaction mixture was diluted with water and extracted with ether. The organic layer was washed with water, dried and evaporated under reduced pressure to give an oily cis-1,2-diformylmethyl-4,4-ethylenedioxy-cyclopentane.

IR $\nu_{max}^{film}$; 1725 cm$^{-1}$
NMR $\delta$(CDCl$_3$); 3.8, 9.7 ppm

EXAMPLE 2

A solution of 8,8-ethylenedioxy-cis-bicyclo[4,3,0]-non-3-ene (1.0 g) in methanol (50 ml) was cooled to $-50°$ C. and subjected to a stream of ozonized oxygen. After the starting material had disappeared, 35 ml of dimethylsulfide was added and the mixture was stirred for 2 hr at $-5° \sim -15°$ C.

The mixture was then concentrated by introduction of a stream of nitrogen to give an oily cis-1,2-diformyl-methyl-4,4-ethylenedioxy-cyclopentane.

The spectral data of the product coincided with that of example 1.

EXAMPLE 3

A solution of the cis-1,2-diformylmethyl-4,4-diethylenedioxy-cyclopentane (1.1 g) in methanol (30 ml) was cooled to $-50°$ C. and treated with 5% aqueous potassium hydroxide, and further stirred at the same temperature. After 4 hr, a saturated solution of sodium chloride and ethylacetate was added to the mixture.

The organic layer was separated, washed with water, dried and concentrated under reduced pressure at a low temperature to give an oily 2-$\beta$-formyl-3-$\alpha$-hydroxy-7,7-ethylenedioxy-cis-bicyclo[3,3,0]octane as a main product.

IR $\nu_{max}^{film}$; 3400, 1710 cm$^{-1}$
NMR $\delta$(CDCl$_3$); 3.85, 9.75 ppm

EXAMPLE 4

The dialdehyde (1.0 g) obtained above (example 1 or 2) was dissolved in methanol (30 ml) and cooled at $-15° \sim -5°$ C.

A 5% aqueous solution (10 ml) of potassium hydroxide was added, and the mixture was stirred for 13 min. at the same temperature.

The mixture was treated as shown in the example 3 to give an oily 2-$\beta$-formyl-3-$\alpha$-hydroxy-7,7-ethylene-dioxy-cis-bicyclo[3,3,0]octane as a main product.

EXAMPLE 5

The dialdehyde (0.7 g) obtained above (example 1 or 2) was dissolved in methanol (17 ml). To this solution was added 5% aqueous barium hydroxide at $0° \sim 10°$ C.

After 1 hr at the same temperature, stirring was continued for 40 hr at a room temperature. The mixture was worked up as shown in example 3 or 4 to give an oily 2-$\beta$-formyl-3-$\alpha$-hydroxy-7,7-ethylenedioxy-cis-bicy-clo[3,3,0]octane. The spectral data coincided with that of example 3 and there was much less content of the isomer.

REFERENCE EXAMPLE 1

A solution of 2-$\beta$-formyl-3-$\alpha$-hydroxy-7,7-ethylenedioxy-bicyclo[3,3,0]octane (23.3 g) in tetrahydrofuran (30 ml) was added into a tetrahydrofuran solution of ylid prepared with dimethyl 2-oxoheptylphosphonate (29.1 g) and sodium hydride (65% mineral oil dispersion, 4.83 g) and the mixture was stirred for 2 hr at room temperature. Evaporation of the solvent gave an oily residue, to which ether and water was added. The ether layer was separated and dried over magnesium sulfate. The solvent was evaporated and the residue was chromatographed on silica gel to give 2-$\beta$-(3'-oxo-trans-1'-octenyl)-3-$\alpha$-hydroxy-7,7-ethylenedioxy-bicyclo[3,3,-0]octane (19.9 g) as an oil.

IR $\nu_{max}^{film}$; 3400, 1670, 1630 cm$^{-1}$
NMR $\delta$(CDCl$_3$); 6.68; 6.03; 3.83 ppm

REFERENCE EXAMPLE 2

A methanolic solution of 2$\beta$-(3'-oxo-trans-1'-octenyl)-3$\alpha$-hydroxy-7,7-ethylenedioxy-bicyclo[3,3,-0]octane (19.9 g) was treated with sodium borohydride (7.4 g) with ice cooling.

Stirring was continued for 2 hr and excess reducing agent was quenched with acetone, and then the mixture was concentrated under reduced pressure. To the residue was added aqueous ammonium chloride and extracted with ethylacetate.

The organic layer was dried and evaporated to give an oily 2$\beta$-(3'-hydroxy-trans-1'-octenyl)-3$\alpha$-hydroxy-7,7-ethylenedioxy-bicyclo[3,3,0]octane (18 g).

The alcohol obtained above was dissolved into a mixed solvent of acetic acid, water and tetrahydrofuran (3:1:1).

The mixture was warmed at 45° C. and stirred for 4 hr. The solvent was evaporated under reduced pressure and the residue was chromatographed on silica gel to give 2$\beta$-(3'$\beta$-hydroxy-trans-1'-octenyl)-3$\alpha$-hydroxy-bicyclo[3,3,0]octane-7-one and 2$\beta$-(3'$\alpha$-hydroxy-trans-1'-octenyl)-3$\alpha$-hydroxy-bicyclo[3,3,0]octane-7-one.

3'$\beta$-hydroxy isomer
IR $\nu_{max}^{film}$; 3400, 1740 cm$^{-1}$
NMR $\delta$(CDCl$_3$); 5.60, 0.9 ppm 3'$\alpha$-hydroxy isomer
IR $\nu_{max}^{film}$; 3400, 1740 cm$^{-1}$
NMR $\delta$(CDCl$_3$); 5.53; 0.9 ppm

REFERENCE EXAMPLE 3

A solution of sodium methylsulfinylmethide, prepared from 65% sodium hydride (1.86 g) and dimethylsulfoxide (30 ml), was cooled to $15° \sim 20°$ C. and treated with 4-carboxybutyl triphenylphosphonium bromide (11.23 g) under nitrogen.

The mixture was stirred for 10 min at 20° C. To the above ylid solution was added a dimethylsulfoxide solution of 2$\beta$-(3'$\alpha$-hydroxy-trans-1'-octenyl)-3$\alpha$-hydroxy-bicyclo[3,3,0]octa-7-one (0.84 g) at $20° \sim 25°$ C. The reaction mixture was stirred for 6 hr at room temperature, and then diluted with water.

The aqueous solution was washed with ether, acidified with aqueous potassium bisulfate and extracted with ethylacetate.

The extract was washed with brine, dried and concentrated in vacuo to give the residue (2.5 g). The residue was chromatographed on silica gel to give 2$\beta$-(3'$\alpha$-hydroxy-trans-1'octenyl)-3$\alpha$-hydroxy-7E-(4'-carboxybutylidene)-bicyclo[3,3,0]octane and 2$\beta$-(3'$\alpha$- hydroxy-trans-1'-octenyl)-3α-hydroxy-7Z-(4'-carboxybutylidene)-bicyclo[3,3,0]octane.

7E isomer

IR δ$_{max}$$^{film}$; 3350, 2650, 1710 cm$^{-1}$

NMR δ(CDCl$_3$); 5.65~5.4 (2H), 5.1~5.4 (1H), 4.6~4.9 (3H)

7Z isomer

IR ν$_{max}$$^{film}$; 3350, 2600, 1710 cm$^{-1}$

NMR δ(CDCl$_3$); 5.7~5.45 (2H), 5.0~5.4 (4H)

What we claim is:

1. A process for producing a compound of the formula:

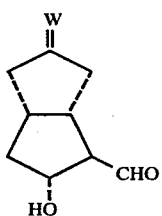

wherein C=W is a carbonyl group or a protected carbonyl group which comprises reacting a compound of the formula:

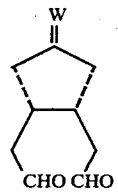

wherein C=W is as defined above in the presence of an acid or a base at a temperature ranging from −70° C. to room temperature.

2. A process according to claim 1 wherein C=W is a protected carbonyl group.

3. A process according to claim 1 wherein the said base is an alkali hydroxide.

4. A process according to claim 1, wherein the protected carbonyl group is an ethylenedioxy group, an ethylenedithio group, a 1,3-propanedioxy group, a 2,2-dimethyl-1,3-propanedioxy group, a 1,2-phenylenedioxy group or two methoxy groups.

* * * * *